(12) United States Patent
Hsu et al.

(10) Patent No.: US 8,188,004 B2
(45) Date of Patent: May 29, 2012

(54) ORGANIC HERBICIDE

(75) Inventors: Hsinhung John Hsu, Ventura, CA (US);
Sergejs Trusovs, Ventura, CA (US);
Franz R. Fernandez, Ventura, CA (US)

(73) Assignee: JH Biotech, Inc., Ventura, CA (US)

( * ) Notice: Subject to any disclaimer, the term of this patent is extended or adjusted under 35 U.S.C. 154(b) by 166 days.

(21) Appl. No.: 12/595,068

(22) PCT Filed: May 10, 2008

(86) PCT No.: PCT/US2008/063351
§ 371 (c)(1),
(2), (4) Date: Oct. 8, 2009

(87) PCT Pub. No.: WO2008/141252
PCT Pub. Date: Nov. 20, 2008

(65) Prior Publication Data
US 2010/0197497 A1    Aug. 5, 2010

Related U.S. Application Data

(60) Provisional application No. 60/917,110, filed on May 10, 2007.

(51) Int. Cl.
| | |
|---|---|
| *A01N 63/00* | (2006.01) |
| *A01N 47/28* | (2006.01) |
| *A01N 41/10* | (2006.01) |
| *A01N 31/02* | (2006.01) |
| *A01N 65/00* | (2009.01) |
| *A01N 25/02* | (2006.01) |
| *A01N 36/00* | (2006.01) |
| *A01N 37/00* | (2006.01) |
| *A61K 36/54* | (2006.01) |
| *A61K 36/00* | (2006.01) |
| *A61K 31/185* | (2006.01) |

(52) U.S. Cl. ........ 504/118; 504/148; 504/162; 504/189; 504/362; 424/725; 424/739; 424/776; 514/578

(58) Field of Classification Search .................. 504/118, 504/148, 162, 189, 362; 424/725, 739, 776; 514/578
See application file for complete search history.

(56) References Cited

U.S. PATENT DOCUMENTS 6,831,107 B2 *   12/2004   Dederen et al. ............... 514/777

OTHER PUBLICATIONS

Bainard et al., "Phytotoxicity of clove oil and its primary constituent eugenol and the role of leaf epicuticular wax in the susceptibility to these essential oils," (2006), Weed Science, 54(5):833-837.*
Tworkowski, T., "Herbicidal effects of essential oils," (2002), Weed Science, 50(4):425-431.*
"Carrier Oils, Essential Oils Differences: Shop for the right base oil," (Copyright 2007); http://www.homeremediescures.com/aromatherapy/carrier-oils.html; pp. 1-5.*
Bainard et al., "Phytotoxicity of clove oil and its primary constituent eugenol and the role of leaf epicuticular wax in the susceptibility to these essential oils," (2006), Weed Science, 54(5): 833-837.*
Tworkoski, T., "Herbicidal effects of essential oils," (2002), Weed Science, 50(4):425-431.*
"Carrier Oils, Essential Oils Differences: Shop for the right base oil," [online], Home Remedies, 2007 [retrieved on Jul. 29, 2011] Retrieved from the Internet: <URL: http://www.homeremediescures.com/aromatherapy/carrier-oils.html>.*

* cited by examiner

*Primary Examiner* — James H. Alstrum-Acevedo
*Assistant Examiner* — Jane C Oswecki
(74) *Attorney, Agent, or Firm* — Ralph D. Chabot

(57) ABSTRACT

An organic herbicide is disclosed and comprises oxidized natural oils such as clove oil, and cinnamon oil. A natural surfactant is disclosed comprising 30-50% by weight casein, 50-70% by weight whole egg powder and 0-5% by weight Konjac glucomannan.

20 Claims, No Drawings

ORGANIC HERBICIDE

CROSS REFERENCE TO RELATED APPLICATIONS

This application claims the benefit of U.S. provisional patent application Ser. No. 60/917,110 filed May 10, 2007, the content of which is hereby incorporated by reference herein in its entirety for all purposes.

FIELD OF THE INVENTION

The present invention relates to an organic herbicide and an organic surfactant that can be used as part of an herbicidal composition.

BACKGROUND OF THE INVENTION

All herbicides and herbicidal compositions may be classified into groups such as artificial or synthetic herbicides and natural herbicides which contain plant oil combinations as a subset. The larger classification, i.e., synthetic or artificial herbicides include, for example, 2, 4-D or Glyphosate, which is primarily used for weed control. However, synthetic herbicides are not permitted for use in applications such as organic farming.

As mentioned above, organic plant oil herbicides can be classified as natural herbicides. These organic herbicides are typically represented by combinations of several plant oils including clove oil, citronella oil and cinnamon oil.

It is also well-known to those skilled in the art that the effectiveness of organic herbicides remarkably improves when the organic herbicidal composition includes organic acids. For example, products sold under the trademarks Burn-Out® II Natural Weed and Grass Killer manufactured by St. Gabriel Laboratories Corp., Gainesville, Va. US; and Matran® EC, manufactured by EcoSmart Technologies, Inc., Franklin, Tenn. US; both contain clove oil and vinegar (acetic acid) and/or citric acid. NATURE'S AVENGER®, manufactured by Cutting Edge Formulations, Inc., Buford, Ga., US is an organic herbicide based on citrus oil. It is known that the improved effectiveness of the natural oil based herbicides cited above results from the acidification occurring to the natural oils. Stated another way, the combination of an acid with natural oils results in a more effective herbicide than natural oils alone.

SUMMARY OF THE INVENTION

The present invention discloses an improved natural oil herbicide which is more effective than prior-art natural oil herbicides for controlling growth of unwanted vegetation or weeds. The natural oil herbicide contains aromatic compounds found in the natural oils which have been oxidized. It is oxidation which creates a more potent herbicide than non-oxidized natural oils. An organic surfactant is also disclosed which can be used effectively as part of an organic herbicide composition. The organic herbicidal composition comprises an effective amount of an oxidized essential oil(s) with a novel natural surfactant which yields a synergistically superior organic herbicide relative to prolonged herbicidal effectiveness when compared to the use of standard surfactants with an organic herbicide.

The term "comprising" when used in the context of a claim means leaving a claim open for inclusion of unspecified ingredients.

The term "consisting of" when used in the context of a claim means closing a claim to inclusion of materials other than those recited except for impurities ordinarily associated therewith.

The term "consisting essentially of" when used in the context of a claim means rendering a claim open only for inclusion of unspecified ingredients that do not materially affect the basic and novel characteristics of the composition.

The inventors have found that oxidation remarkably increases the potency of essential oils and effectiveness as an herbicide.

The term "oxidized essential oils" used in accordance with the invention are oxidized clove oil, oxidized cinnamon oil and mixtures thereof. Other essential oils, namely those containing the compound eugenol, are also to be included.

The term "effective concentration" is defined as a concentration of oxidized essential oils in a volume of water so that the diluted composition can be used as an herbicide. In other words, the volume of carrier added is not so excessive as to reduce the potency of the composition below an acceptable level.

It is to be understood that the organic herbicidal composition will further comprise a surfactant, and preferably, the natural surfactant which will be discussed in further detail below.

Oxidation of the essential oils can be accomplished using at least one of the many well-known procedures available either in the presence of, or without a catalyst(s).

Suitable oxidizing agents can be air, oxygen, ozone, organic and inorganic peroxides, nitrates, perchlorates, chlorates, hypochlorites, chromates, dichromates, permanganates, persulfates, and any other substance known to those skilled in the art of being a suitable oxidizer. Each group of oxidizing agents requires a separate methodology to perform an oxidation process.

If an organic herbicide, the subject of our invention, contains two or more essential oils, oxidizing each essential oil separately or in combination, will result in a more effective herbicide than if no oxidation step had been performed. Therefore, the present invention provides an improved organic herbicide by oxidizing the essential oil components.

The primary chemical constituents of clove oil are eugenol, eugenol acetate, iso-eugenol and caryophyllene. The primary chemical constituents of cinnamon oil are eugenol, eugenol acetate, cinnamic aldehyde and benzyl benzoate. These constituents are members of the group of so called substituted aromatic compounds and are thus capable of being oxidized.

According to a further aspect of our invention the organic herbicide comprising an effective amount of oxidized essential oil such as clove oil, cinnamon oil or mixture thereof, that can be emulsified into a liquid carrier. Thus advantageously, the concentrated organic herbicide having a natural surfactant component can be supplied in a convenient storage form and thereafter diluted with a suitable amount of water for subsequent application, such as spray application or the like.

The organic herbicide made according to our invention is particularly effective against broad leaved weed species such as docks, nettles and thistles. It is also particularly effective against common ragwort which is toxic to livestock.

Preparation of Organic Herbicide with Natural Surfactant

There has always been a long sought need for manufacture of natural "organic" herbicides i.e., herbicides that are completely based on the natural constituents and more importantly, organic herbicides that approach the effectiveness of synthetic herbicides but that are environmentally safe.

Traditionally, all oil-containing agricultural products consist of three main constituents: oil(s), water and surfactant(s).

Attempts to use known organic surfactants such as stearic acid, saponin, lecithin, and combinations thereof have not been successful. Oil and water phase separation occurs which is detrimental to creating an effective, long-lasting herbicide.

An organic herbicide having a natural surfactant has been developed that provides a highly stable oil-water emulsion. This stability translates into an herbicide, which after foliar application, remains longer on the plants and thus remains an effective herbicide for a longer duration.

Our composition combines two food products, namely casein (milk protein) and whole egg powder which together act as a natural surfactant. It is known in the art that casein and whole egg powder, separately have been used as surfactants. However, an emulsion created using either casein or whole egg powder separately is of a limited duration. It has been discovered that combining casein and whole egg powder for use as a surfactant extends the duration of an emulsion synergistically longer than for those emulsions created by using casein or whole egg powder separately.

More preferably, adding Konjac (Konjac glucomannan) significantly increases the duration of the stabilized emulsion by increasing the viscosity. Thus, a preferred embodiment for our natural surfactant comprises 30-50% by weight casein, 30-50% by weight whole egg powder and 0-5% Konjac (Konjac glucomannan). A highly desired stable oil-water emulsion is formed when the above-mentioned oxidized essential oil composition is combined with water. In a most preferred embodiment, the composition for our natural surfactant is a composition which consists essentially of: 30-50% by weight casein (milk protein); 50-70% by weight whole egg powder; and 0-5% by weight Konjac (Konjac glucomannan).

Although the natural surfactant can be sold separately, when a concentrated organic herbicide is to include the surfactant, an amount of water is necessary to be added and be considered part of the concentrated mix, due to the fact that whole egg powder and casein are water soluble. The preferable composition of the concentrated organic herbicide contains a range of constituents between 60-72% oxidized essential oils, 3-6% natural surfactant and 22-37% water.

Thereafter, the concentrated organic herbicide is diluted for spray or foliar application. The dilution composition preferably has between 3-10% oxidized essential oils.

BEST MODE FOR CARRYING OUT THE INVENTION

The present invention may be more clearly understood with reference to the accompanying examples, which are purely exemplary.

The following examples are presented to illustrate the most common methods for oxidizing essential oils for use as an organic herbicide. Oxidation by: 1) air; 2) oxygen; 3) hydrogen peroxide; and, 4) sodium hypochlorite. Other methods for oxidation that have not been disclosed but are capable of providing the necessary oxidation step for a natural herbicide are also contemplated to be covered by our invention.

Example 1

Oxidation by Air

Combine 66 grams clove oil and 34 grams cinnamon oil into a jacketed vertical glass reactor having a porous bottom for providing and dispersing air blown into the reactor. The reaction mass is thereafter heated to 70-80° C. Air is continuously blown through the oil solution for 1-15 hours. During this time, oxidation occurs changing the color of the oils from bright yellow-brown to dark brown. The reaction mass is allowed to cool.

Example 2

Oxidation by Oxygen

Combine 66 grams clove oil and 34 grams cinnamon oil into a jacketed vertical glass reactor having a porous bottom for providing and dispersing oxygen blown into the reactor. The reaction mass is thereafter heated to 50-70° C. Oxygen is continuously blown through the oil solution for 0.5-8 hours. During this time, oxidation occurs changing the color of the oils from bright yellow-brown into dark brown. The reaction mass is allowed to cool.

Example 3

Oxidation by Air in the Presence of Catalyst

Combine 66 grams clove oil and 34 grams cinnamon oil into a jacketed vertical glass reactor having a porous bottom for providing and dispersing air blown into the reactor. Add 3% by weight oxidation catalyst comprised of 1% Platinum on activated carbon powder. The reaction mass is thereafter heated to 70-80° C. Air is continuously blown through the oil solution for 0.5-6 hours. During this time, oxidation occurs changing the color of the oils from bright yellow-brown to dark brown. Separate the catalyst by sedimentation and allow the reaction mass to cool.

Example 4

Oxidation by Hydrogen Peroxide in the Presence of Catalyst

Combine 66 grams clove oil and 34 grams cinnamon oil into a jacketed vertical glass reactor having a high rate propeller stirrer and begin stirring. Add 1% by weight iron sulfate as catalyst. Heat the reaction mass to 30-50° C. Add 35% hydrogen peroxide−10% of the mass of oils slowly to the mixture. When all the hydrogen peroxide has been added, continue stirring the reaction mass for 1 additional hour, then cool. Separate the water layer.

Example 5

Oxidation by Sodium Hypocholorite

Combine 66 grams clove oil and 34 grams cinnamon oil into a jacketed vertical glass reactor having a high rate propeller stirrer and begin stirring. Heat the reaction mass to 40-50° C. Add 15% by weight sodium hypochlorite water solution (traditional laundry bleach) slowly to the mixture. When all the sodium hypochlorite has been added, continue stirring the reaction mass for 1 additional hour, then cool. Separate the water layer.

Once oxidation is complete, the oxidized oils are ready for processing into the concentrated organic herbicide.

As mentioned earlier, although oxidizing essential oils yield a more effective organic herbicide than if no oxidation occurred, the lack of a suitable surfactant or emulsifier limits the effective duration of the herbicide following application.

As shown experimentally, the new surfactant not only provides good stability to the herbicidal composition based on the oxidized oils but also prolongs its herbicidal activity remarkably increasing the time of for weed re-growth on the treated areas as illustrated in the table below.

Example 6

Preparation of Herbicidal Composition with Natural Surfactant 33.6 grams water was pumped inside a tank having a high speed propeller stirrer. 0.1 grams Konjac (Konjac glucomannan) was added and stirred for 20-30 min or until completely dissolved. Thereafter, 2.5 grams whole egg powder and 1.6 grams milk casein were added and stirred for 20-30 min until a relatively viscous solution is obtained. Afterwards, slowly added to the slurry is 62 grams of oxidized oil component which is then stirred for an additional 15-20 min until a consistent emulsion is obtained.

Example 7

Preparation of Herbicidal Composition Based on Synthetic Surfactant 90 grams by weight oxidized oils comprising 66% clove oil and 34% cinnamon oil and 10 grams synthetic surfactant were added and stirred for 15-20 min at ambient conditions until a consistent viscosity was obtained.

Testing (Herbicide Field Tests)

Field tests were conducted on 5 replicates with each replicate being a 6'×6' block area on Marathon Sod. Test was a randomized complete block design and of 14 days duration. Treatments were applied to foliage with a pressure backpack sprayer, and each replicate received between 0.6-0.7 gal of treatment. The following compositions were compared during this test.

Formula 1—based on a non-oxidized mixture of clove oil and cinnamon oil with a synthetic surfactant having equal parts of NP-95, SI-80 and SI-20 (see Example 7).

Formula 2—based on an oxidized clove oil and cinnamon oil composition oxidized by air (see Example 1) and the natural surfactant (see Example 6).

Formula 3—based on an oxidized clove oil and cinnamon oil composition oxidized using hydrogen peroxide (see Example 4) and the natural surfactant composition blended in Example 6.

Formula 4—0.67% hydrogen peroxide and 99.33% water.

Formula 5—0.67% synthetic surfactant and 99.33% water.

Formula 6—containing organic surfactant (39% casein and 61% whole egg). Surfactant concentration in the spray 0.67%.

Formula 7—the oxidized oil and synthetic surfactant mixture of Example 7.

Formula 8—non-oxidized oils, namely 66% clove oil and 34% cinnamon oil and the natural surfactant composition blended in Example 6.

All formulas having oils were diluted with water for foliar application. The concentration of essential oils in the diluted composition was 6% by weight.

The control formula was 100% water.

TABLE

| Herbicide | Average results | | | | |
|---|---|---|---|---|---|
| | Day 1 | Day 3 | Day 7 | Day 10 | Day 14 |
| Control | 0 | 0 | 0 | 0 | 0 |
| Formula 1 | 47 | 93 | 85 | 73 | 68 |
| Formula 2 | 50 | 93 | 88 | 85 | 83 |
| Formula 3 | 49 | 100 | 95 | 95 | 95 |
| Formula 4 | 0 | 0 | 0 | 0 | 0 |
| Formula 5 | 0 | 0 | 0 | 0 | 0 |
| Formula 6 | 0 | 0 | 0 | 0 | 0 |
| Formula 7 | 50 | 82 | 85 | 79 | 75 |
| Formula 8 | 50 | 93 | 88 | 85 | 83 |

(% burn, 0% = no burn, 100% = completely burn)

From the above testing, the following conclusions can be drawn:
1. surfactants by themselves, including hydrogen peroxide (formulas 4, 5, and 6) did not exhibit any herbicidal effectiveness.
2. the natural surfactant disclosed achieved higher effectiveness over a longer period of time than formulations using a synthetic surfactant.

We claim:

1. A concentrated organic herbicide comprising:
   at least one oxidized essential oil selected from the group consisting of: oxidized clove oil, oxidized cinnamon oil, oxidized eugenol and mixtures thereof: and,
   where hydrogen peroxide is used to oxidize an essential oil selected from the group consisting of: clove oil, cinnamon oil, eugenol and mixtures thereof; into said at least one oxidized essential oil.

2. The concentrated organic herbicide of claim 1 further comprising a natural surfactant comprising 30-50% by weight casein, 50-70% by weight whole egg powder.

3. The concentrated organic herbicide of claim 2 where said natural surfactant further comprises 0-5% by weight Konjac glucomannan.

4. The concentrated organic herbicide of claim 3 further comprising water sufficient to solubilize said surfactant, said concentrated organic herbicide comprising between 60-72% said at least one oxidized essential oil, 3-6% surfactant and 22-37% water.

5. The concentrated organic herbicide of claim 4 diluted with water to form a dilution composition containing an effective concentration of organic herbicide.

6. The dilution composition of claim 5 where the dilution composition contains between 3-10% by weight said at least one oxidized essential oil.

7. A concentrated organic herbicide comprising:
   at least one oxidized essential oil selected from the group consisting of: oxidized clove oil, oxidized cinnamon oil, oxidized eugenol and mixtures thereof;
   where an oxidizing agent selected from the group consisting of: organic peroxides, inorganic peroxides, nitrates, perchlorates, chlorates, hypochlorites, chromates, dichromates, permanganates, and persulfates is used to oxidize an essential oil selected from the group consisting of: clove oil, cinnamon oil, eugenol and mixtures thereof; into said at least one oxidized essential oil and,
   a natural surfactant consisting essentially of 30-50% by weight casein, 50-70% by weight whole egg powder.

8. The concentrated organic herbicide of claim 7 where said natural surfactant further comprises 0-5% by weight Konjac glucomannan.

9. The concentrated organic herbicide of claim 8 further comprising water sufficient to solubilize said surfactant, said concentrated organic herbicide comprising between 60-72% at least one oxidized essential oil, 3-6% surfactant and 22-37% water.

10. The concentrated organic herbicide of claim 9 diluted with water to form a dilution composition containing an effective concentration of organic herbicide.

11. The dilution composition of claim 10 where the dilution composition contains between 3-10% by weight at least one essential oil.

12. A natural surfactant comprising 30-50% by weight casein, 50-70% by weight whole egg powder and 0-5% by weight Konjac glucomannan.

13. A concentrated organic herbicide comprising:
at least one oxidized essential oil selected from the group consisting of: oxidized clove oil, oxidized cinnamon oil, eugenol and mixtures thereof; where hydrogen peroxide was used to oxidize an essential oil selected from the group consisting of: clove oil, cinnamon oil, eugenol and mixtures thereof; into said at least one oxidized essential oil;
a natural surfactant comprising 30-50% by weight casein, 50-70% by weight whole egg powder; and,
water sufficient to solubilize said surfactant, said concentrated organic herbicide comprising between 60-72% by weight at least one oxidized essential oil, 3-6% by weight surfactant and 22-37% by weight water.

14. The concentrated organic herbicide of claim 13 where said natural surfactant further comprises 0-5% by weight Konjac glucomannan.

15. The concentrated organic herbicide of claim 13 diluted with water to form a dilution composition containing an effective concentration of organic herbicide.

16. The dilution composition of claim 13 where the dilution composition contains between 3-10% by weight at least one oxidized essential oil.

17. The concentrated organic herbicide of claim 1 where a catalyst is used to form said at least one oxidized essential oil.

18. The concentrated organic herbicide of claim 17 where said catalyst is iron sulfate.

19. The concentrated organic herbicide of claim 7 where a catalyst is used to form said at least one oxidized essential oil.

20. The concentrated organic herbicide of claim 13 where a catalyst is used to form said at least one oxidized essential oil.

\* \* \* \* \*